US009733178B2

(12) United States Patent
Ryu et al.

(10) Patent No.: US 9,733,178 B2
(45) Date of Patent: Aug. 15, 2017

(54) SPECTRAL ELLIPSOMETRY MEASUREMENT AND DATA ANALYSIS DEVICE AND RELATED SYSTEMS AND METHODS

(71) Applicant: Samsung Electronics Co., Ltd., Suwon-si, Gyeonggi-do (KR)

(72) Inventors: Sung-Yoon Ryu, Hwaseong-si (KR); Woo-Seok Ko, Seoul (KR); Yu-Sin Yang, Seoul (KR); Sang-Kil Lee, Yongin-si (KR); Chung-Sam Jun, Suwon-si (KR)

(73) Assignee: Samsung Electronics Co., Ltd. (KR)

( * ) Notice: Subject to any disclaimer, the term of this patent is extended or adjusted under 35 U.S.C. 154(b) by 167 days.

(21) Appl. No.: 14/806,775

(22) Filed: Jul. 23, 2015

(65) Prior Publication Data

US 2016/0025618 A1   Jan. 28, 2016

(30) Foreign Application Priority Data

Jul. 24, 2014 (KR) .......................... 10-2014-0093959

(51) Int. Cl.
*G01N 21/21* (2006.01)
*G01N 21/95* (2006.01)
G01N 21/956 (2006.01)

(52) U.S. Cl.
CPC ....... *G01N 21/211* (2013.01); *G01N 21/9501* (2013.01); *G01N 21/956* (2013.01); *G01N 2021/213* (2013.01)

(58) Field of Classification Search
CPC ........................ G01N 2021/213; G01N 21/211
(Continued)

(56) References Cited

U.S. PATENT DOCUMENTS 5,706,212 A * 1/1998 Thompson ................ G01J 4/00
  250/339.09
5,872,630 A * 2/1999 Johs ........................ G01J 3/447
  250/225

(Continued)

FOREIGN PATENT DOCUMENTS

JP         2013-197537         9/2013

*Primary Examiner* — Kara E Geisel
*Assistant Examiner* — Violeta A Prieto
(74) *Attorney, Agent, or Firm* — Ward and Smith, P.A.

(57) ABSTRACT

Spectral ellipsometry measurement systems are provided including a polarizer that rotates at a first angle and adjusts a polarizing direction of incident light of a measurement sample; a compensator that rotates at a second angle, different from the first angle, and adjusts a phase difference of the incident light; an analyzer that rotates at a third angle and adjusts a polarizing direction of light reflected on the measurement sample; a detector that detects a spectral image from the reflected light; a controller that controls one of the polarizer, the compensator, and the analyzer according to polarizer-compensator-analyzer (PCA) angle sets including the first to third angles; and a processor that receives, from the detector, a first spectral image corresponding to a first PCA angle set and a first wavelength and a second spectral image corresponding to a second PCA angle set and a second wavelength, different from the first wavelength, and generates a polarizer-compensator-analyzer rotating (PCAR) spectral matrix using the first and second spectral images.

16 Claims, 21 Drawing Sheets

(58) Field of Classification Search
USPC .......................................................... 356/369
See application file for complete search history.

(56) References Cited

U.S. PATENT DOCUMENTS

| | | | |
|---|---|---|---|
| 6,353,477 B1 * | 3/2002 | Johs | ................ G01J 3/447 356/369 |
| 7,369,233 B2 | 5/2008 | Nikoonahad et al. | |
| 7,369,235 B1 | 5/2008 | Janik et al. | |
| 7,869,040 B1 | 1/2011 | Kwak et al. | |
| 7,889,339 B1 | 2/2011 | Flock et al. | |
| 8,126,694 B2 | 2/2012 | Liu et al. | |
| 8,279,431 B2 | 10/2012 | Hirose et al. | |
| 8,446,584 B2 | 5/2013 | Krishnan et al. | |
| 2012/0287433 A1 * | 11/2012 | Krishnan | ........... G01B 11/0641 356/327 |
| 2013/0010296 A1 | 1/2013 | Kwak et al. | |
| 2013/0248975 A1 | 9/2013 | Hishida et al. | |
| 2015/0219497 A1 * | 8/2015 | Johs | .................. G01J 4/02 356/367 |

\* cited by examiner (Cube A)

(Cube B)

(Cube C)

(Cube N)

SPECTRAL ELLIPSOMETRY MEASUREMENT AND DATA ANALYSIS DEVICE AND RELATED SYSTEMS AND METHODS

CROSS-REFERENCE TO RELATED APPLICATION

This application claims priority from Korean Patent Application No. 10-2014-0093959, filed Jul. 24, 2014 in the Korean Intellectual Property Office, the contents of which are hereby incorporated herein by reference as if set forth in its entirety.

FIELD

The present inventive concept relates generally to spectral ellipsometry and, more particularly, to spectral ellipsometry measurement and data analysis.

BACKGROUND

A semiconductor device is manufactured using a wafer through several hundreds of manufacturing operations. Therefore, after performing various operations for manufacturing the semiconductor device on the wafer, resultant products of the manufacturing process steps are inspected or measured within a short time.

As the semiconductor manufacturing process is becoming highly integrated, development of 3D profile measuring techniques of semiconductor micro patterns or complex structures is under way. In recently developed memory and logic products, wafers are fabricated using micro processing technology with a linewidth of 20 nm or less, and a technique for monitoring high-speed micro-patterning is required to improve the yield and quality of wafers. Process failure inspection and profile measurement techniques are largely divided into an optical method and an electron beam method. Of the two methods, the optical method has a more advantageous inspection speed. However, according to the recent trend toward patterning with a linewidth of less than the optical resolution level, the traditional optical method imposes a limitation in 3D profile measurement. To address this issue, an optical critical dimension (OCD) technique is proposed to extract a profile through electromagnetic analysis of the light scattered from micro patterns and may be applied to 3D profile analysis.

SUMMARY

Some embodiments of the inventive concept provide a spectral ellipsometry measurement system for extracting a polarizer-compensator-analyzer (PCA) angle set and wavelength band reacting most sensitively to measurement variables by analyzing spectrums acquired from various PCA angle sets.

In further embodiments, a method for spectral ellipsometry measurement for extracting the PCA angle set and wavelength band reacting most sensitively to measurement variables by analyzing spectrums acquired from various PCA angle sets is provided.

Still further embodiments provided a data analysis device for spectral ellipsometry measurement for extracting the PCA angle set and wavelength band reacting most sensitively to measurement variables by analyzing spectrums acquired from various PCA angle sets.

Some embodiments provide a spectral ellipsometry measurement system including a polarizer rotating at a first angle and adjusting a polarizing direction of incident light of a measurement sample, a compensator rotating at a second angle and adjusting a phase difference of the incident light, an analyzer rotating at a third angle and adjusting a polarizing direction of light reflected on the measurement sample, a detector detecting a spectral image from the reflected light, a controller controlling the polarizer, the compensator, or the analyzer according to PCA angle sets including the first to third angles, and a processor receiving from the detector a first spectral image corresponding to a first PCA angle set and a first wavelength and a second spectral image corresponding to a second PCA angle set and a second wavelength different from the first wavelength and generating a polarizer-compensator-analyzer rotating (PCAR) spectral matrix using the first and second spectral images.

Further embodiments of the present inventive concept provide a method for spectral ellipsometry measurement, the method including providing a measurement sample having a predetermined value set with respect to measurement variables, based on PCA angle sets including first to third angles, handling the first angle of a polarizer adjusting a polarizing direction of incident light of the measurement sample, the second angle of a compensator adjusting a phase difference of the incident light, and the third angle of an analyzer adjusting a polarizing direction of light reflected from the measurement sample, extracting a first spectral image and a second spectral image from the reflected light, the first spectral image corresponding to a first PCA angle set and a first wavelength and the second spectral image corresponding to a second PCA angle set and a second wavelength different from the first wavelength, and generating a PCAR spectral matrix using the first and second spectral images.

Still further embodiments provide a data analysis device including a processor, and a first storage unit receiving input data and storing a data analysis module for deducing PCA angle sets and wavelength bands under optimal conditions for measurement variables using the processor, wherein the input data includes a PCAR spectral matrix, the PCAR spectral matrix is generated using a first spectral image and a second spectral image, the first spectral image corresponding to a first PCA angle set and a first wavelength and the second spectral image corresponding to a second PCA angle set and a second wavelength different from the first wavelength, each of the first and second PCA angle sets includes a first angle for adjusting a polarizing direction of incident light of the measurement sample, a second angle for adjusting a phase difference of the incident light, and a third angle for adjusting a polarizing direction of light reflected from the measurement sample, the deducing of the PCA angle sets and wavelength bands under optimal conditions for the measurement variables comprises deducing spectrums representing a change in the light intensity in each pixel depending on wavelengths using the PCAR spectral matrix, and selecting the PCA angle set and wavelength band under optimal conditions for measurement variables using the spectrums.

Some embodiments of the present inventive concept provide a data analysis method including providing input data including a PCAR spectral matrix, deducing spectrums representing a change in the light intensity in each pixel depending on wavelengths using the PCAR spectral matrix using a processor, and selecting the PCA angle sets and wavelength bands under optimal conditions for measurement variables through a spectrum analysis algorithm using the processor, wherein the PCAR spectral matrix includes data about the PCA angle sets and wavelength bands for each pixel, and the spectrum analysis algorithm includes a correlation analysis algorithm for measuring a similarity between the spectrum extracted from the PCAR spectral matrix and an ideal spectrum and a principal component analysis algorithm for selecting the wavelength band having the largest displacement of the measurement variables in the extracted spectrum.

BRIEF DESCRIPTION OF THE DRAWINGS

The above and other features and advantages of the present inventive concept will become more apparent by describing in detail preferred embodiments thereof with reference to the attached drawings in which.

DETAILED DESCRIPTION OF THE EMBODIMENTS

Figure 1:
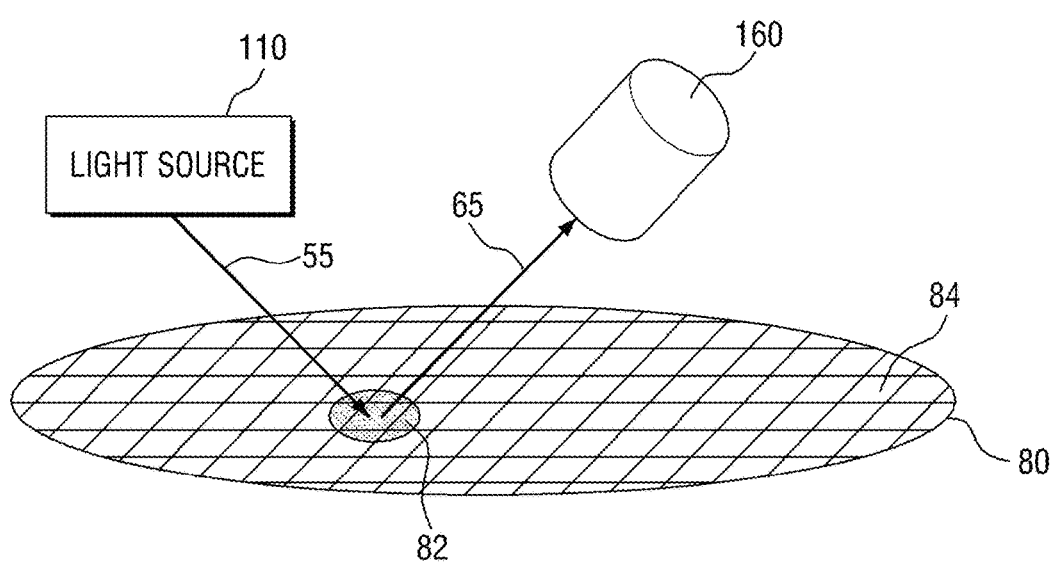
FIG. 1 is a diagram illustrating a wafer inspection method according to some embodiments of the present inventive concept.

Advantages and features of the present inventive concept and methods of accomplishing the same may be understood more readily by reference to the following detailed description of preferred embodiments and the accompanying drawings. The present inventive concept may, however, be embodied in many different forms and should not be construed as being limited to the embodiments set forth herein. Rather, these embodiments are provided so that this disclosure will be thorough and complete and will fully convey the concept of the inventive concept to those skilled in the art, and the present inventive concept will only be defined by the appended claims. Like reference numerals refer to like elements throughout the specification.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that when an element or layer is referred to as being "on", "connected to" or "coupled to" another element or layer, it can be directly on, connected or coupled to the other element or layer or intervening elements or layers may be present. In contrast, when an element is referred to as being "directly on", "directly connected to" or "directly coupled to" another element or layer, there are no intervening elements or layers present. As used herein, the term "and/or" includes any and all combinations of one or more of the associated listed items.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present inventive concept.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Embodiments are described herein with reference to cross-section illustrations that are schematic illustrations of idealized embodiments (and intermediate structures). As such, variations from the shapes of the illustrations as a result, for example, of manufacturing techniques and/or tolerances, are to be expected. Thus, these embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present inventive concept.

Unless otherwise defined, all terms (including technical and scientific terms) used herein have the same meaning as commonly understood by one of ordinary skill in the art to which the present inventive concept belongs. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

Some embodiments of the present inventive concept provide a spectral ellipsometry measurement system and related method and data analysis device as will be discussed herein with respect to FIGS. 1 to 20 below.

Referring first to FIG. 1, a diagram illustrating a wafer inspection method according to some embodiments of the present inventive concept will be discussed. As illustrated in FIG. 1, the wafer inspection method according to some embodiments of the present inventive concept includes inspecting a wafer 80 using a spectral image sensing method. First, incident light 55 is irradiated from a light source 110 into a measuring area 82 on the wafer 80. Various manufacturing processing steps may be performed on the wafer 80 to form a plurality of areas, for example, chip areas 84. The measuring area 82 may include a single chip area 84 or a plurality of chip areas 84 according to the incidence range of the incident light 55. The wafer inspection method according to some embodiments of the present inventive concept allows spectral ellipsometry (SE) data for a plurality of positions to be measured at a time.

The incident light 55 irradiated into the wafer 80 is reflected at the measuring area 82 on the wafer 80 and the light 65 reflected at the measuring area 82 may be incident into the detector 160. The detector 160 may be, for example, a spectral imaging camera, but aspects of the present inventive concept are not limited thereto. The detector 160 may detect spectral images from the reflected light 65 that has been incident thereto which will be discussed further below.

Figure 2:
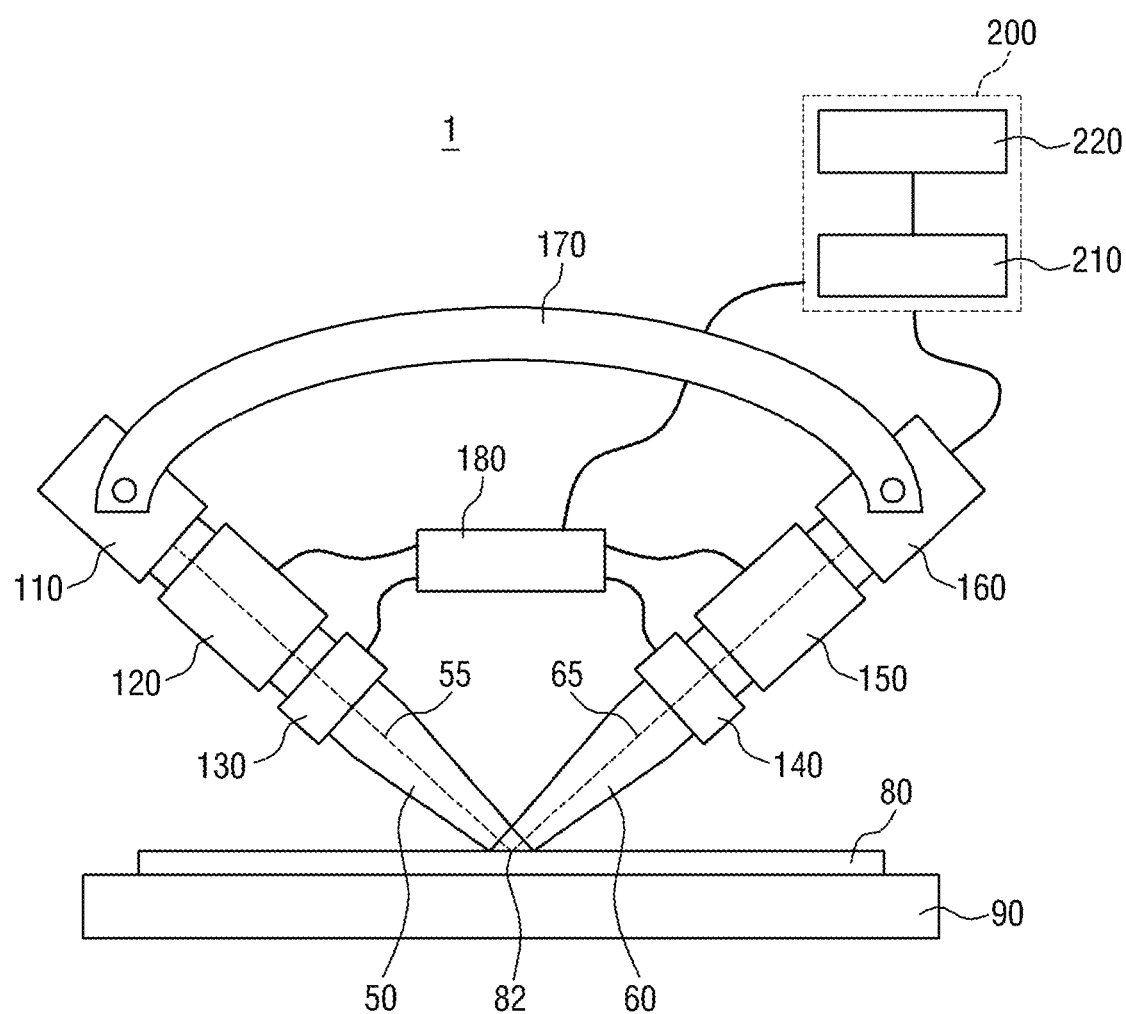
FIG. 2 is a block diagram of a spectral ellipsometry measurement system according to some embodiments of the present inventive concept.

Referring now to FIG. 2, a block diagram of a spectral ellipsometry measurement system according to some embodiments of the present inventive concept will be discussed. As illustrated in FIG. 2, the spectral ellipsometry measurement system 1 according to some embodiments of the present inventive concept includes a wafer 80, a tray 90, a light source 110, a polarizer 120, a compensator 130, an analyzer 140, an imaging lens 150, a detector 160, a controller 180, an angle handler 170, and a processor 200.

The wafer 80 may have the measuring area 82. The wafer 80 may be, for example, a semiconductor substrate. The wafer 80 may include, for example, silicon (Si), strained Si, a silicon alloy, silicon carbide (SiC), silicon germanium (SiGe), silicon germanium carbide (SiGeC), germanium, a germanium alloy, gallium arsenide (GaAs), indium arsenide (InAs), one of III-V group semiconductor compounds, one of II-VI group semiconductor compounds, and stacks thereof without departing from the scope of the present inventive concept. Furthermore, the wafer 80 may be an organic plastic substrate, rather than a semiconductor substrate. The wafer 80 may be positioned on the tray 90.

The tray 90 may be used to mount the wafer 80. The tray 90 may fix a position of the wafer 80 or may move the wafer 80 to a particular position during the semiconductor manufacturing process. For example, the tray 90 may move the wafer 80 in a first direction or a second direction perpendicular to the first direction, but aspects of the present inventive concept are not limited thereto.

The light source 110 may emit broadband light. For example, the light source 110 may irradiate visible light. In these embodiments, the visible light may have a wavelength band in a range of 400 nm to 800 nm, but aspects of the present inventive concept are not limited thereto. The wavelength band of the light source 110 may vary according to the object to be measured, and the light source 110 may generally have a bandwidth ranging from a UV band to an NIR band. The light source 110 may emit light having a particular wavelength or may simultaneously emit light having various wavelengths. The polarizer 120 or the compensator 130 may be disposed along the path of the incident light 55 emitted from the light source 110, and the incident light 55 may move within the entrance body 50. In other words, the incident light 55 may be irradiated into the measuring area 82 of the wafer 80 placed on the tray 90 through the polarizer 120 or the compensator 130.

The wavelength band of the light source 110 may be related to the detector 160. The light source 110 may use wavelength bands over multiple band ranges because its sensitivity to the measuring area 82 of the wafer 80 differs according to the wavelength band of the light source 110, but aspects of the present inventive concept are not limited thereto.

The entrance body 50 may fix positions of the light source 110, the polarizer 120, and the compensator 130 and may extend in the same direction with the path of the incident light 55.

The polarizer 120 may adjust a polarizing direction of the incident light 55. The polarizer 120 may include a rotation part capable of adjusting the polarizing direction and may rotate at a first angle. The polarizer 120 may receive the incident light 55 from the light source 110. The polarizer 120 may be electrically connected to the controller 180. The controller 180 may control the first angle of the polarizer 120.

The compensator 130 may adjust a phase difference of the incident light 55. Although not clearly shown, the compensator 130 may include a rotation part and may rotate at a second angle. The compensator 130 may adjust the phase difference of the incident light 55 using the rotation part. The compensator 130 may be electrically connected to the controller 180. The controller 180 may control the second angle of the compensator 130. The compensator 130 may be connected to the light source 110 or the polarizer 120 through the entrance body 50.

The incident light 55 emitted from the light source 110 may be irradiated into the measurement sample 22 placed on the wafer 80 and the reflected light 65 reflected into the measurement sample 22 may move within the emission body 60.

The emission body 60 may fix positions of the analyzer 140, the imaging lens 150, and the detector 160 and may extend in the same direction with the path of the reflected light 65. An incidence angle of the incident light 55 and a reflection angle of the reflected light 65 may be the same with each other, but aspects of the present inventive concept are not limited thereto.

The analyzer 140 may adjust a polarizing direction of the reflected light 65 reflected to the measurement sample 22. The analyzer 140 may include a rotation part and may rotate at a third angle. The analyzer 140 may be electrically connected to the controller 180. The controller 180 may control the third angle of the analyzer 140.

The imaging lens 150 may control chromatic aberration of the reflected light 65. The imaging lens 150 may be positioned between the analyzer 140 and the detector 160. The imaging lens 150 may have a focal distance f, and the focal distance f may be inversely proportional to a distance between the imaging lens 150 and the measurement sample 22 and may be proportional to a distance between the imaging lens 150 and the detector 160, but aspects of the present inventive concept are not limited thereto. The imaging lens 150 may also be connected to the controller 180, and the controller 180 may control the focal distance f by varying the position of the imaging lens 150, but aspects of the present inventive concept are not limited thereto.

The detector 160 may detect spectral images from the reflected light 65. For example, the detector 160 may detect a spectral image with respect to a particular wavelength. Although not clearly shown, the detector 160 may include a photo sensor (not shown) capable of sensing the reflected light 65. The reflected light 65 may be incident into the photo sensor (not shown) at a first angle, and the first angle may not be a right angle, but aspects of the present inventive concept are not limited thereto.

The angle handler 170 may handle the incidence angle of the incident light 55 and the reflection angle of the reflected light 65. In particular, the angle handler 170 may be connected to one side of the entrance body 50 and one side of the emission body 60. The angle handler 170 may handle angles of the entrance body 50 and the emission body 60. The angle handler 170 may be controlled by the controller 180 or the processor 200, but aspects of the present inventive concept are not limited thereto.

The controller 180 may be connected to the polarizer 120, the compensator 130, the analyzer 140, the imaging lens 150, and the processor 200. The controller 180 may receive polarizer-compensator-analyzer (PCA) angle sets from the processor 200. The PCA angle sets may include first to third angles. The controller 180 may control the first angle of the polarizer 120, the second angle of the compensator 130 and the third angle of the analyzer 140 according to the received PCA angle sets, but aspects of the present inventive concept are not limited thereto. The controller 180 may generate the first to PCA angle sets by varying the first to third angles according to predetermined values. For example, the controller 180 may generate the plurality of PCA angle sets while varying the second angle of the compensator 130 after setting the first angle of the polarizer 120 and the third angle of the analyzer 140.

The processor 200 may receive a spectral image (20 of FIG. 4) from the detector 160. The processor 200 may generate a polarizer-compensator-analyzer rotating (PCAR) spectral matrix (30 of FIG. 5) using the received spectral image (20 of FIG. 4). For example, the processor 200 may receive from the detector 160 a first spectral image corresponding to a first PCA angle set and a first wavelength and a second spectral image corresponding to a second PCA angle set and a second wavelength different from the first wavelength and may generate the PCAR spectral matrix (30 of FIG. 5) using the first and second spectral images, but aspects of the present inventive concept are not limited thereto. The detector 160 may be a spectral imaging camera.

In particular, processor 200 may include a first processing device 210 and a second processing device 220, but aspects of the present inventive concept are not limited thereto. As illustrated in FIG. 2, the processor 200 includes a first processing device 210 and a second processing device 220. However, it will be understood that embodiments of the present inventive concept are not limited to this configuration. For example, the first processing device 210 and the second processing device 220 may be configured to be separate from each other or more than two processing devices may be provided without departing from the scope of the present inventive concept.

The first processing device 210 may convert the first and second spectral images detected from the detector 160 into the PCAR spectral matrix (30 of FIG. 5) and may store the same. The PCAR spectral matrix (30 of FIG. 5) will be discussed further below. The first processing device 210 may generate spectrums (40 of FIG. 6) representing a change in the light intensity from each pixel using the PCAR spectral matrix (30 of FIG. 5). The first processing device 210 may be connected to the second processing device 220 and may generate the spectrums (40 of FIG. 6) when there is a request from the second processing device 220. The first processing device 210 may be a data readout computer, but aspects of the present inventive concept are not limited thereto.

The second processing device 220 may analyze the generated the spectrums (40 of FIG. 6) from the first processing device 210 and may select the PCA angle sets and wavelength bands under optimal or near optimal conditions for measurement variables. The second processing device 220 may be a data analyzer 140 or an optical critical dimension (OCD) meter including a spectrum analysis algorithm. The OCD meter may extract physical parameters in the measuring area of the wafer 80 from spectral data. The spectrum analysis algorithm of the OCD meter may include a rigorous coupled-wave analysis (RCWA) algorithm. The RCWA algorithm may be advantageously used in accounting for diffraction or reflection of electromagnetic waves from a surface of a lattice structure, but aspects of the present inventive concept are not limited thereto.

The second processing device 220 may employ spectroscopic ellipsometry or multi-point high-speed spectroscopic ellipsometry for monitoring a profile change in the wafer 80. Furthermore, the second processing device 220 may perform variable separation algorithms for extracting profile changes from multiple spectrums, including correlation analysis algorithm, principal component analysis algorithm, rank test, and so on, which will be discussed further below.

The spectral ellipsometry measurement system 1 may measure measurement variables, including, for example, critical dimension, a pattern height, recess, overlay, defect, and the like.

The spectral ellipsometry measurement system 1 according to some embodiments of the present inventive concept may detect the PCA angle sets and wavelength bands under optimal or near optimal conditions, which react most sensitively to measurement variables. The spectral ellipsometry measurement system 1 acquires the PCA angle sets and wavelength bands under optimal or near optimal conditions for each measurement variable and then uses the acquired PCA angle sets and wavelength bands in monitoring the measurement variables, thereby identifying the change in the measurement variables at high speed.

Figure 3:
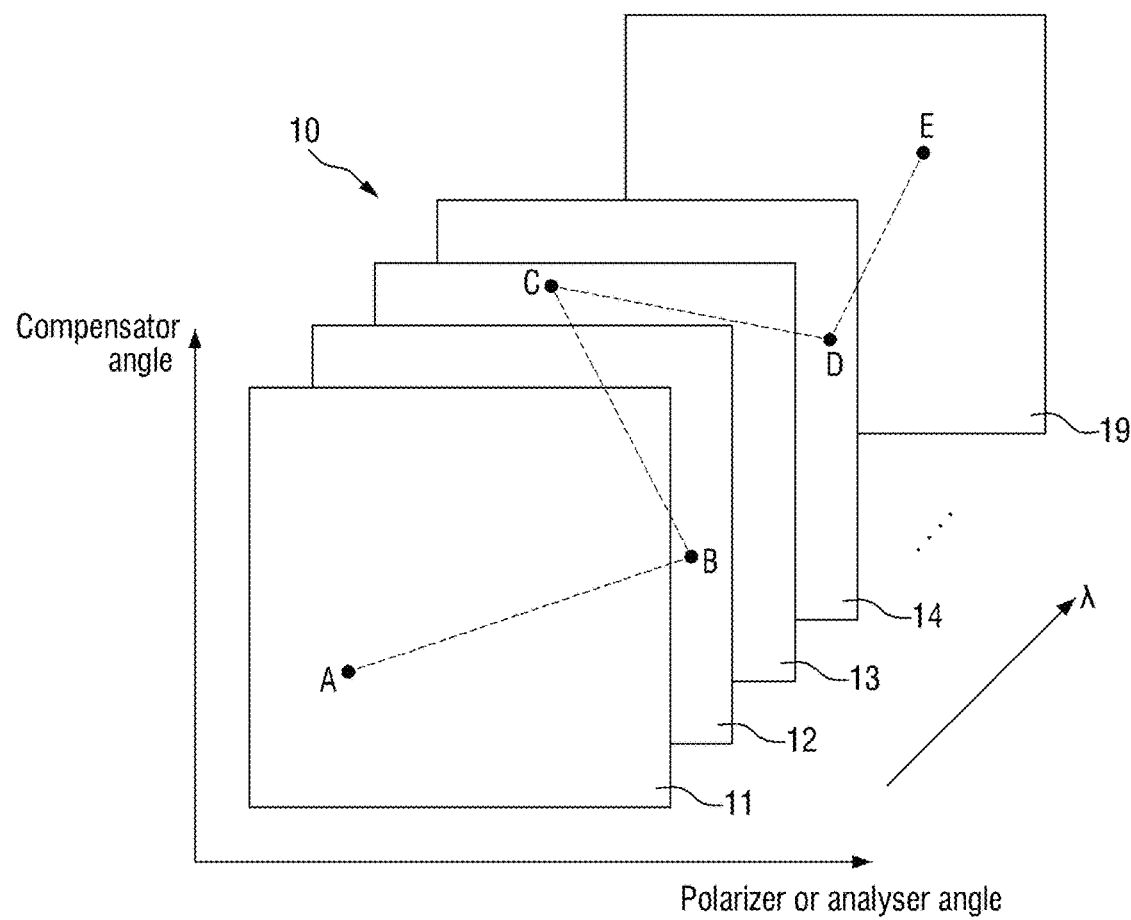
FIG. 3 is a diagram illustrating images of polarizer-compensator-analyzer (PCA) angle sets for wavelengths according to some embodiments of the present inventive concept.
Figure 4:
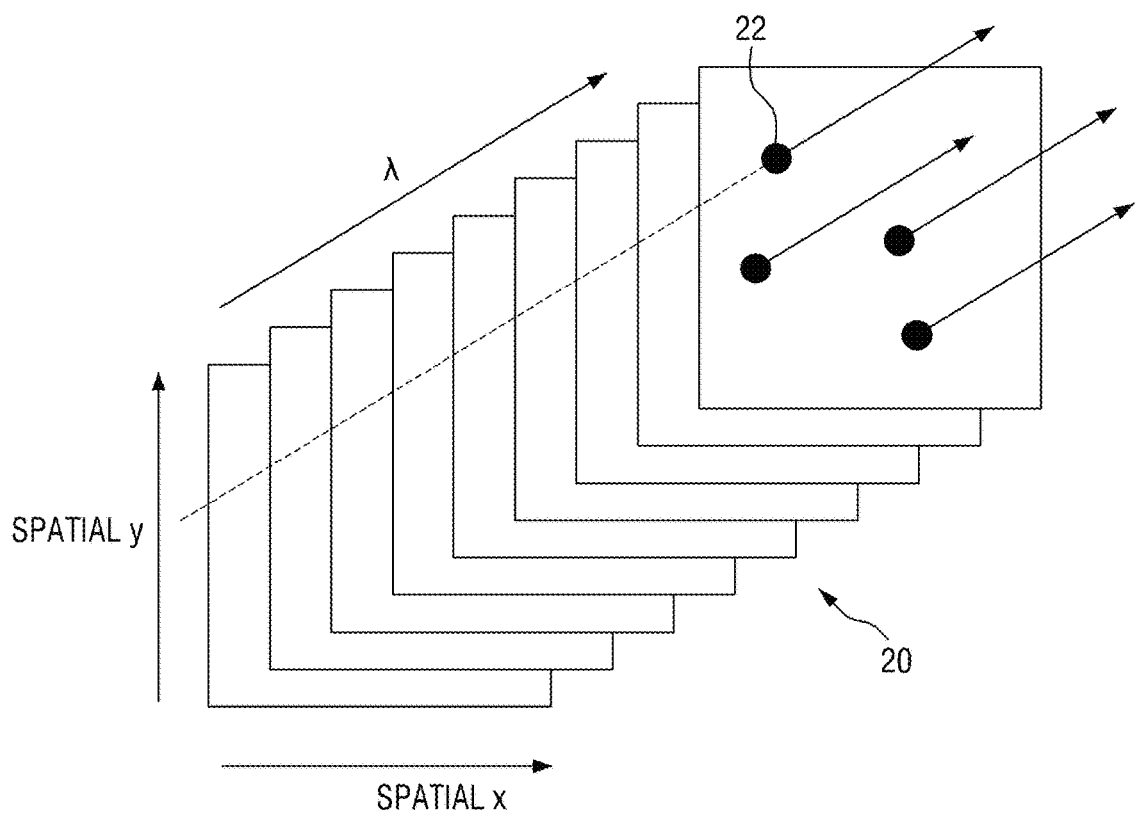
FIG. 4 is a diagram illustrating spectral images for wavelengths according to some embodiments of the present inventive concept.
Figure 5:
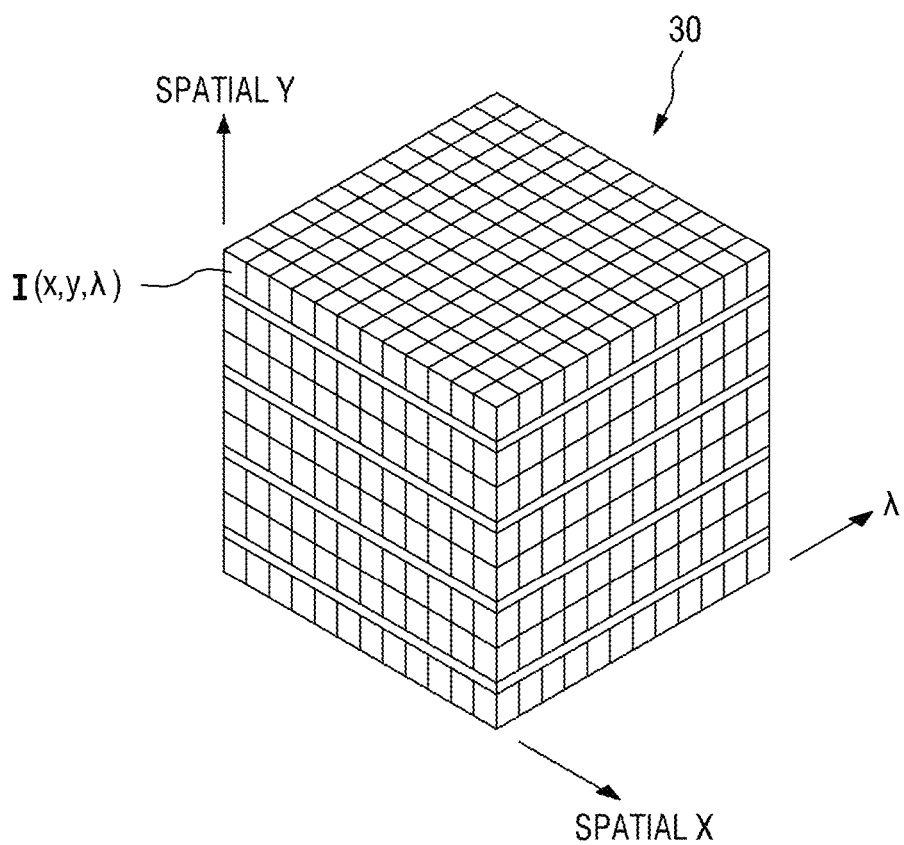
FIG. 5 is a diagram illustrating a polarizer-compensator-analyzer rotating (PCAR) spectral matrix according to some embodiments of the present inventive concept.
Figure 6:
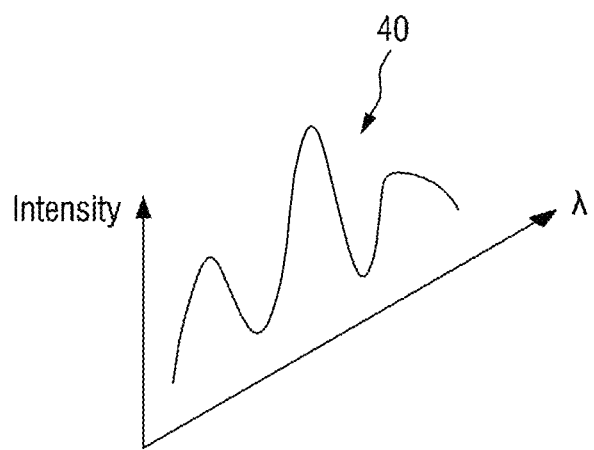
FIG. 6 is a diagram illustrating spectrums of each pixel in the PCAR spectral matrix shown in FIG. 5.
Figure 7A:
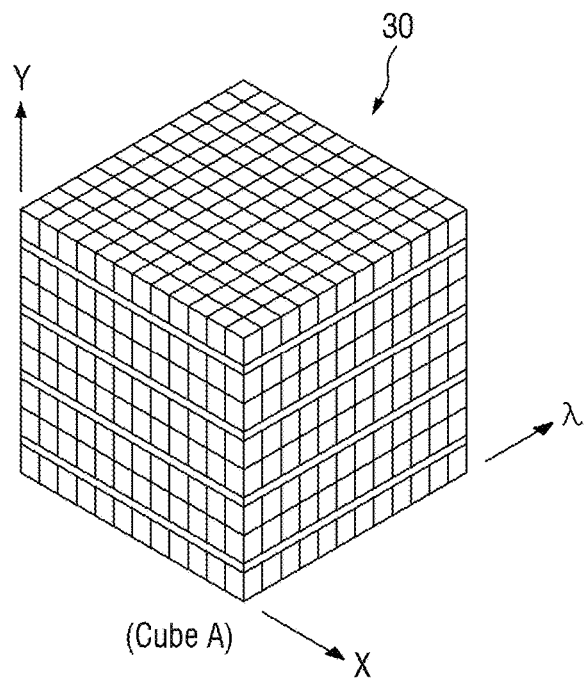
FIGS. 7A through 7D are diagrams illustrating a plurality of PCAR spectral matrixes having different PCA angle sets in accordance with some embodiments of the present inventive concept.
Figure 7B:
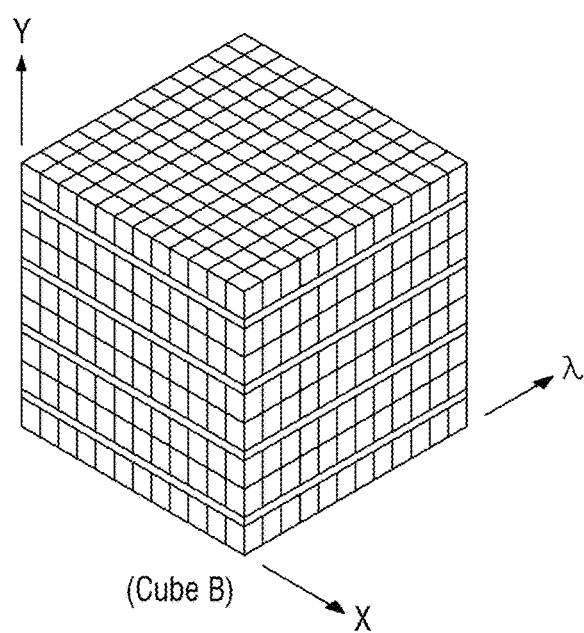
Figure 7C:
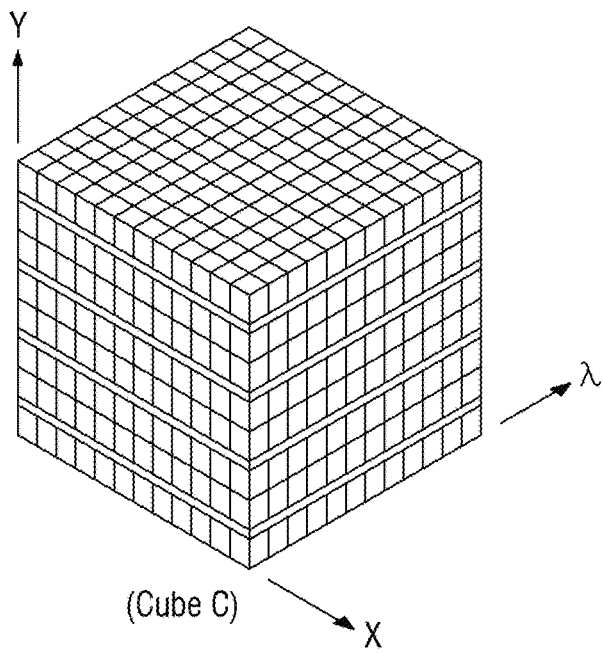
Figure 7D:
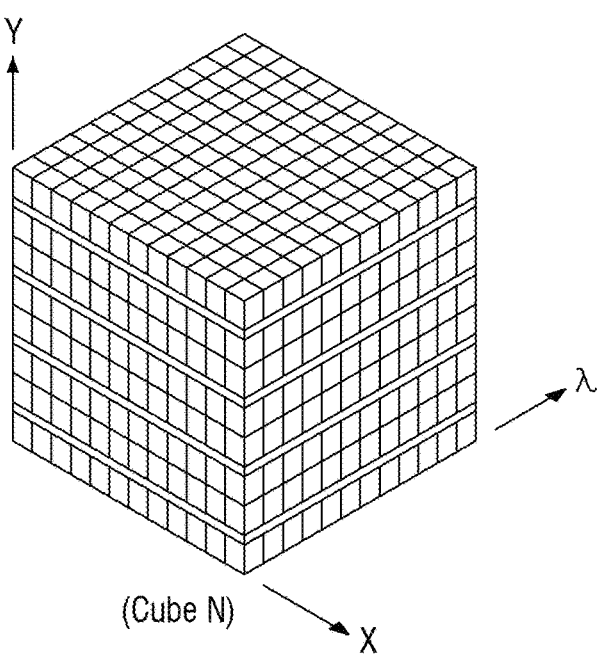
Figure 8:
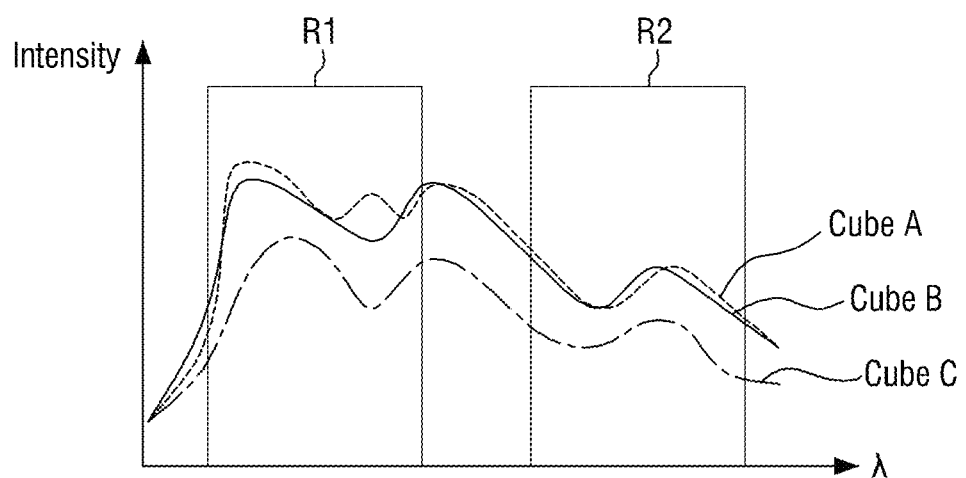
FIG. 8 is a diagram illustrating spectrums of particular pixels extracted from the plurality of PCAR spectral matrixes shown in FIG. 7.

FIG. 3 is a diagram illustrating images of PCA angle sets for wavelengths according to some embodiments of the present inventive concept. FIG. 4 is a diagram illustrating spectral images for wavelengths according to some embodiments of the present inventive concept. FIG. 5 is a diagram illustrating a PCAR spectral matrix according to some embodiments of the present inventive concept. FIG. 6 is a diagram illustrating spectrums of each pixel in the PCAR spectral matrix shown in FIG. 5. FIG. 7 is a diagram illustrating a plurality of PCAR spectral matrixes having different PCA angle sets. FIG. 8 is a diagram illustrating spectrums of particular pixels extracted from the plurality of PCAR spectral matrixes shown in FIGS. 7A through 7D.

Embodiments of the present inventive concept will now be discussed with respect to these figures. In the spectral ellipsometry measurement system 1 according to some embodiments of the present inventive concept, if the light having polarized components passes through the measurement sample 22, the reflectivity and phase of the light may vary according to the polarizing direction (p or s waves). The spectral ellipsometry measurement system 1 may measure electromagnetic values of p and s waves by varying combinations of the PCA angle sets. The polarizing direction of the light incident into the sample may be determined by the first angle of the polarizer 120 and a phase difference between the p and s waves may be determined by the second angle of the compensator. The polarizing direction of the light incident into the detector 160 after passing through the sample may be determined by the third angle of the analyzer 140.

If a pattern profile at a measuring position is changed due to a processing variation in the semiconductor manufacturing process or a defect, the reflectivity and phase of the measurement sample 22 may change. In these embodiments, a changing tendency of the pattern profile can be detected by varying the PCA angle sets. If the measurement sample 22 has a complex structure, a change in the measurement variables may affect the reflectivity and phase of the measurement sample 22 in multiple, complex manners. Therefore, it is necessary to detect the PCA angle set that is most sensitively affected by the change in the measurement variables. However, it is quite difficult to extract the measurement variables with high sensitivity just by using the PCA angle sets. Therefore, spectral ellipsometric data for each PCA angle set may be used. The reflectivity and phase of each of the p and s waves of the measurement sample 22 vary according to the measurement variables. Thus, in the case of using the spectral ellipsometric data, more measurement variables can be extracted than in the case of using the spectral data.

Referring now to FIG. 3, the spectral ellipsometry measurement system 1 according to some embodiments of the present inventive concept may select a PCA angle set by wavelength with respect to a first measurement variable. For example, different PCA angle sets A, B, C, D and E may be selected for the respective wavelengths λ. The PCA angle sets may be selected randomly, in a predetermined order or by a predetermined algorithm, but aspects of the present inventive concept are not limited thereto.

As illustrated in FIG. 4, spectral images 20 may be measured for the respective PCA angle sets. Each of the spectral images 20 may have data for spatial x and spatially. The PCA angle sets may be selected for the respective wavelengths, and the spectral images 20 corresponding to the PCA angle sets and wavelengths may be measured, respectively. For example, the n spectral images 20 may be measured for the n wavelength λ and the PCA angle sets of the respective spectral images 20 may be different from one another, but aspects of the present inventive concept are not limited thereto.

Referring to FIG. 5, a PCAR spectral matrix 30 is illustrated. The PCAR spectral matrix 30 may be generated in the processor 200 using the plurality of spectral images 20, but aspects of the present inventive concept are not limited thereto. The PCAR spectral matrix 30 may be directly obtained in the detector 160 when the detector 160 measures the reflected light 65. In some embodiments, the PCAR spectral matrix 30 output from the detector 160 may be stored in the first processing device 210 of the processor 200.

The PCAR spectral matrix 30 means a virtual spectral data structure obtained by re-sampling pixels in a spatial area and a spectrum area. The PCAR spectral matrix 30 may be referred to as a spectral cube. The PCAR spectral matrix 30 is composed of spatial axes, as shown in FIG. 5, that is, spatial X and spatial Y and may have a plurality of spectral images 20 depending on wavelength (λ) in a widthwise direction. In other words, the PCAR spectral matrix 30 may include data in the form of a spectral cube having spatial axes of spatial X and spatial Y for a pixel array of the measurement sample 22 and the wavelength (λ). The PCAR spectral matrix 30 may be defined by the coordinate I (x, y, λ).

The spectral images 20 may be defined in a spectral domain. The PCAR spectral matrix 30 may include the spectral images 20 having spatial axes of each pixel 22 photographed by a Field Of View (FOV) of the photo sensor included in the detector 160, and spectrums of the respective pixels 24 depending on the wavelength. In other words, the PCAR spectral matrix 30 may include a plurality of spectral images 20 and spectrums representing a change in the light intensity depending on the wavelengths in the respective pixels 22 of the spectral images 20.

Referring to FIG. 6, a change in the light intensity depending on the wavelengths of the reflected light 65 in each pixel 22 of the spectral images 20, as indicated by arrows in FIG. 4 is illustrated. In FIG. 6, the y axis indicates the intensity and the z axis indicates the wavelength (λ).

Referring to FIGS. 7A through 7D, the spectral ellipsometry measurement system 1 according to some embodiments of the present inventive concept forms a plurality of PCAR spectral matrixes 30 (Cubes A through N) for one measurement sample 22. The forming of the PCAR spectral matrixes 30 may be performed by the processor 200 or the detector 160. Each of the PCAR spectral matrixes 30 may be generated by substantially the same method (as discussed above with respect to FIGS. 3 through 6). The respective PCAR spectral matrixes 30 may have the same data structure. For example, N PCAR spectral matrixes 30 may be generated for the one measurement sample 22, but aspects of the present inventive concept are not limited thereto.

The plurality of PCAR spectral matrixes 30 may be sequentially formed. However, when each of the plurality of PCAR spectral matrixes 30 is formed, the PCA angle sets may be determined randomly or using a predetermined algorithm. In other words, the respective PCAR spectral matrixes 30 may have different combinations of PCA angle sets.

In particular, a first PCAR spectral matrix 30 and a second PCAR spectral matrix 30 may have the same number of spectral images 20. However, the PCA angle set of the first spectral image 20 having the first wavelength included in the first PCAR spectral matrix 30 may be different from the PCA angle set of the second spectral image 20 having the first wavelength included in the second PCAR spectral matrix 30. For example, the first processing device 210 may store the first PCAR spectral matrix 30 and the second PCAR spectral matrix 30 different from the first PCAR spectral matrix 30. In these embodiments, the first PCAR spectral matrix 30 is generated using the first and second spectral images, and the second PCAR spectral matrix 30 is generated using a third PCA angle set different from the first PCA angle set, a third spectral image corresponding to the first wavelength, a fourth PCA angle set different from the second PCA angle set and a fourth spectral images 20 corresponding to the second wavelength, but aspects of the present inventive concept are not limited thereto.

The spectral ellipsometry measurement system 1 according to some embodiments of the present inventive concept may select one among the plurality of PCAR spectral matrixes 30, the selected one varying most sensitively to the measurement variables.

Referring now to FIG. 8, a spectrum for a first pixel of the measurement sample 22 is illustrated. The second processing device 220 may extract spectrums for the first pixel from the plurality of PCAR spectral matrix 30 and may compare the extracted spectrums with one another. From the spectrums shown in FIG. 8, the second processing device 220 may select the PCA angle set and wavelength band, for example, R1 or R2, under optimal conditions, which react most sensitively to the measurement variables. The spectrums shown in FIG. 8, respectively labeled Cubes A to C, may have different PCA angle sets, but aspects of the present inventive concept are not limited thereto.

The second processing device 220 may perform variable separation algorithms for extracting profile changes from multiple spectrums, including correlation analysis algorithm, principal component analysis algorithm, rank test, and the like.

Figure 17:
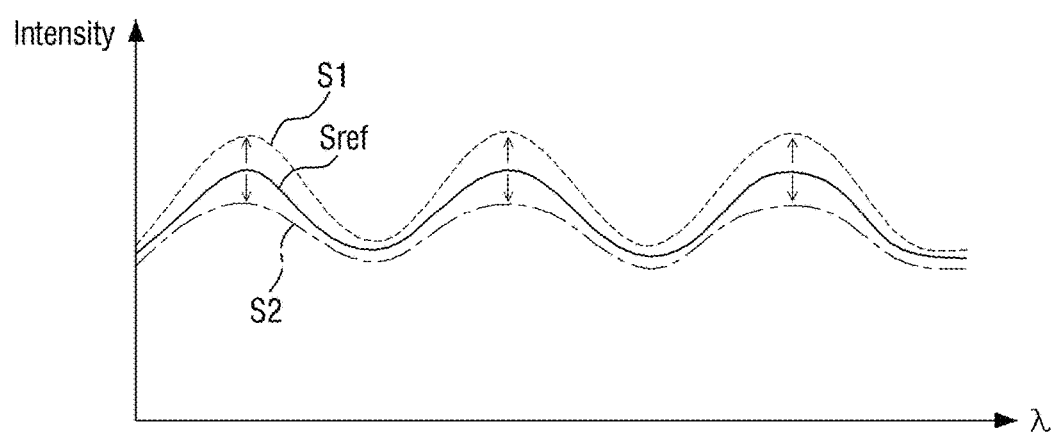
FIG. 17 is a graph for illustrating a correlation analysis algorithm according to some embodiments of the present inventive concept.

The correlation analysis algorithm may be performed for measuring a similarity between the spectrum, for example, S1 or S2 of FIG. 17, extracted from the PCAR spectral matrix 30 and an ideal spectrum, for example, Sref of FIG. 17. The ideal spectrum (Sref of FIG. 17) may be a spectrum for measurement sample 22 predefined by a user. In other words, the measurement sample 22 may be fabricated by the user to satisfy the ideal spectrum (Sref of FIG. 17). The measurement sample 22 may vary according to the measurement variable to be measured, but aspects of the present inventive concept are not limited thereto. A plurality of measurement variables may be handled by a single measurement sample 22.

The principal component analysis algorithm may be performed for selecting the wavelength band having the largest displacement of the measurement variables in the extracted spectrum. If multiple measurement variables demonstrate the optimal sensitivity with respect to the selected PCA angle set and wavelength band under the same condition, the condition may be delicately readjusted to set up independent final conditions for the respective measurement variables. At this stage, a rank test may be employed.

The rank test may be performed to determine whether the PCA angle sets and wavelength bands under the optimal conditions for the plurality of measurement variables overlap or not. If there are overlapping PCA angle sets and wavelength bands under the optimal conditions, measurement may not be properly due to interference among the measurement variables. In these embodiments, the correlation analysis algorithm or the principal component analysis algorithm may be performed again to select the next PCA angle set and wavelength band to avoid interference among the measurement variables.

Local scattering or defects for the respective measurement variables of an image profile can be detected at a high speed by measuring spectral image profiles for other wafers using the selected PCA angle set and wavelength band under the optimal conditions.

Figure 9:
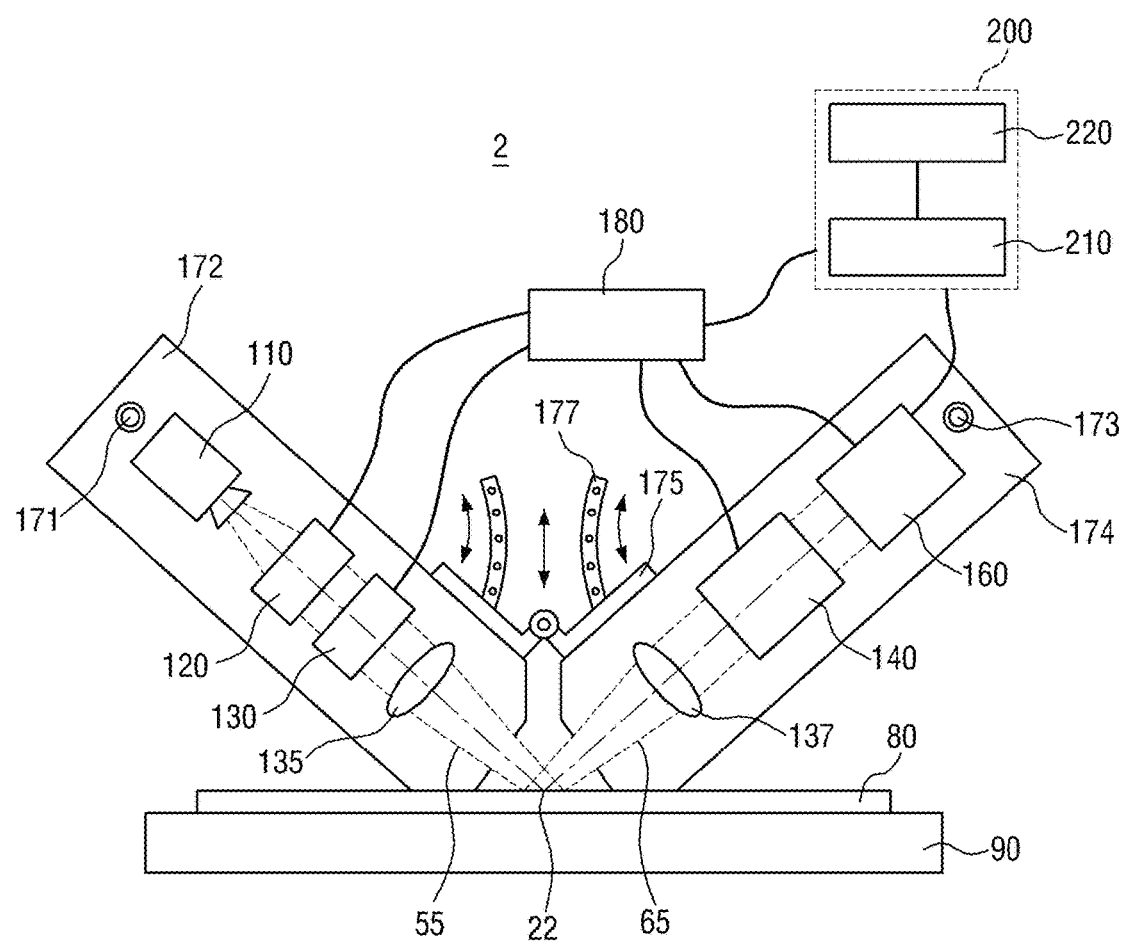
FIG. 9 is a block diagram of a spectral ellipsometry measurement system according to some embodiments of the present inventive concept.

Referring now to FIG. 9, a block diagram of a spectral ellipsometry measurement system according to some embodiments of the present inventive concept will be discussed. For the sake of convenient explanation, details similar to those discussed with respect to embodiments illustrated in FIGS. 1-8 will not be repeated herein. Thus, the following description will focus on differences between the previous and present embodiments.

As illustrated in FIG. 9, the spectral ellipsometry measurement system 2 of FIG. 9 may be formed in substantially the same manner with the spectral ellipsometry measurement system discussed above with respect to FIG. 2. The spectral ellipsometry measurement system 2 may further include a first lens 135, a second lens 137, and an angle handler 170.

In the spectral ellipsometry measurement system 2, a polarizer 120 may be positioned between a light source 110 and a compensator 130. The first lens 135 may be positioned between the compensator 130 and a measurement sample 22. The first lens 135 may change a light path to allow incident light 55 having passed through the compensator 130 to be irradiated on a measuring area 82 of a wafer 80. The measuring area 82 of the wafer 80 may include the measurement sample 22.

The second lens 137 may be positioned between the measurement sample 22 and the analyzer 140. The second lens 137 may change a light path to allow reflected light 65 from the measuring area 82 to be irradiated into the analyzer 140.

The angle handler 170 may include an entrance body 172, an emission body 174, a connection part 175, and a moving rail 177.

The entrance body 172 may include a light source 110, a polarizer 120, a compensator 130, and a first lens 135. The light source 110, the polarizer 120, the compensator 130, and the first lens 135 may be disposed on the path of the incident light 55. Likewise, the emission body 174 may include a second lens 137, an analyzer 140, and a detector 160. The second lens 137, the analyzer 140 and the detector 160 may be disposed on the path of the reflected light 65.

The entrance body 172 and the emission body 174 may be disposed to be symmetrical with each other. The entrance body 172 may move about a first hinge 171. Likewise, the emission body 174 may also rotate about a second hinge 173. The connection part 175 may be connected to one side of the entrance body 172 and one side of the emission body 174 and a connection hinge 176 may be provided at the center of the connection part 175. Angles of the connection part 175 may be changed by the connection hinge 176. The entrance body 172, the emission body 174 and the connection part 175 may move up and down along the moving rail 177. Accordingly, the incidence angle and reflection angle may be changed. Although not clearly shown, the angle handler 170 may be controlled by the controller 180 or the processor 200, but aspects of the present inventive concept are not limited thereto.

Figure 10:
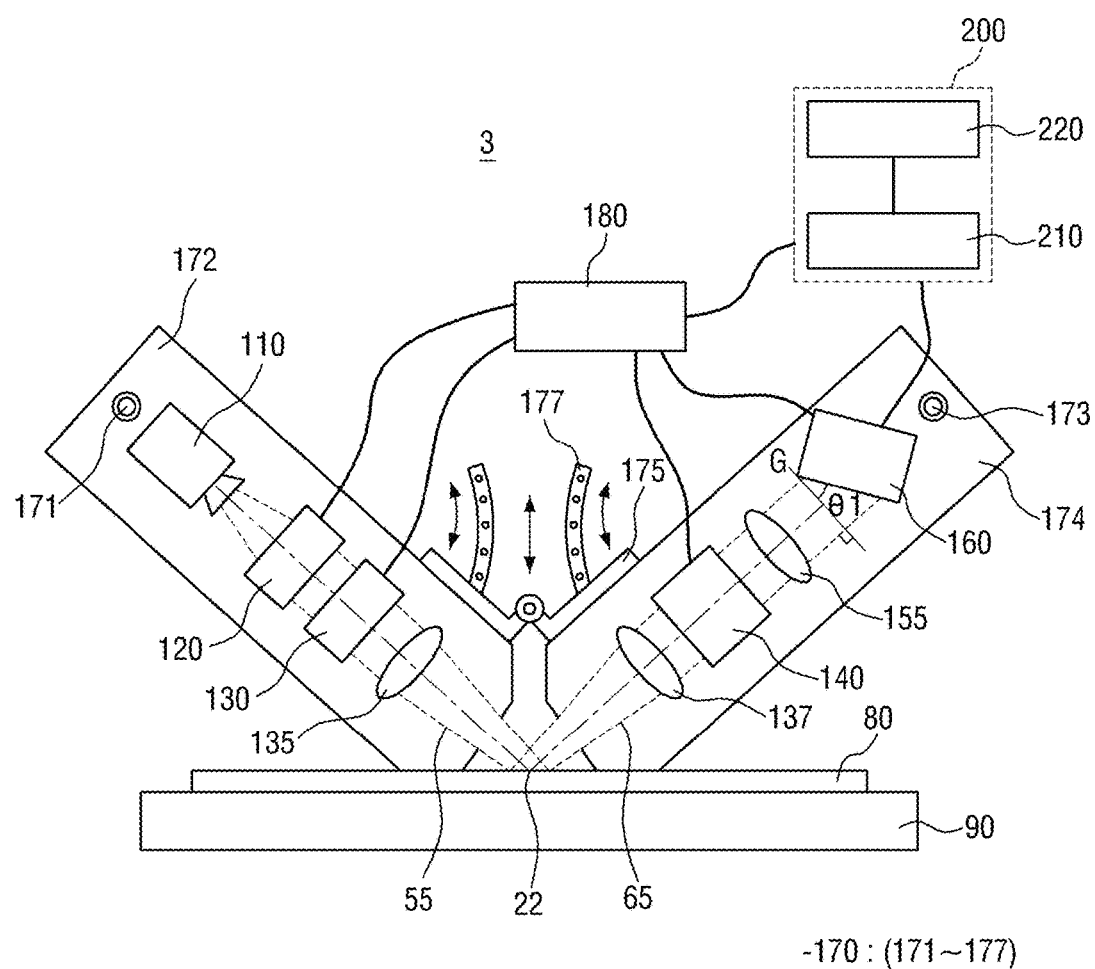
FIG. 10 is a block diagram of a spectral ellipsometry measurement system according to some embodiments of the present inventive concept.

Referring now to FIG. 10, a block diagram of a spectral ellipsometry measurement system according to some embodiments of the present inventive concept will be discussed. For the sake of convenient explanation, details similar to those discussed with respect to embodiments illustrated in FIGS. 1-9 will not be repeated herein. Thus, the following description will focus on differences between the previous and present embodiments.

As illustrated in FIG. 10, the spectral ellipsometry measurement system 3 is substantially the same manner as the spectral ellipsometry measurement system 2 discussed above with respect to FIG. 9. The spectral ellipsometry measurement system 3 may further include an imaging lens 155.

The imaging lens 155 may be positioned between an analyzer 140 and a detector 160. The imaging lens 155 may adjust chromatic aberration of reflected light 65. The imaging lens 155 may have a focal distance f, and the focal distance f may be inversely proportional to a distance between the imaging lens 155 and a measurement sample 22 and may be proportional to a distance between the imaging lens 155 and the detector 160. The imaging lens 155 may also be connected to the controller 180, and the controller 180 may control the focal distance f by varying the position of the imaging lens 155, but aspects of the present inventive concept are not limited thereto.

The reflected light 65 having passed through the imaging lens 155 may be vertically incident into G-line. The detector 160 may be disposed to be tilted with respect to the G-line by a first angle θ1, which is for the purpose of allowing the reflected light 65 to be incident into a photo sensor of the detector 160 at the first angle θ1 or a second angle (90°-θ1), rather than at a right angle. With this configuration, the spectral ellipsometry measurement system 3 according to some embodiments of the present inventive concept may measure Spectral Ellipsometry (SE) data for multiple positions at a time, but aspects of the present inventive concept are not limited thereto.

Figure 11:
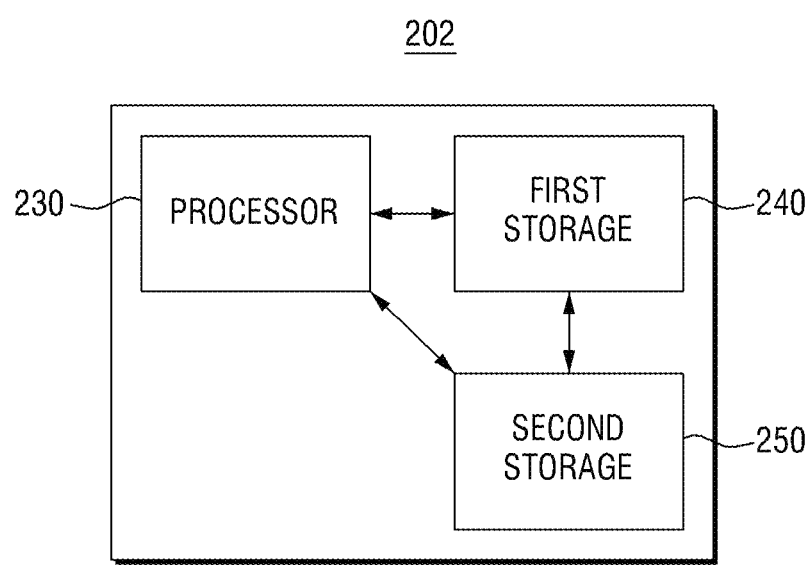
FIG. 11 is a block diagram of a data analysis device according some embodiments of the present inventive concept.

Referring now to FIG. 11, a block diagram of a data analysis device according to some embodiments of the present inventive concept will be discussed. As illustrated in FIG. 11, the data analysis device 202 according to some embodiments of the present inventive concept includes a processor 230, a first storage 240 and a second storage 250.

The processor 230 may perform particular computation operations or tasks. In these embodiments, the processor 230 may include the second processing device 220 according to the previous embodiments. According to some embodiments, the processor 230 may be a micro-processor 230 or a central processing unit (CPU).

The processor 230 may perform communication with the first storage 240 and the second storage 250 through an address bus, a control bus and a data bus. According to some embodiments, the processor 230 may also be connected to an extension bus, such as a peripheral component interconnect (PCI) bus.

The first storage 240 and the second storage 250 may store data necessary for operations of the data analysis device 202. For example, the first storage 240 or the second storage 250 may be implemented as DRAM, mobile DRAM, SRAM, PRAM, FRAM, RRAM and/or MRAM. The first storage 240 and the second storage 250 may include a solid state drive (SSD) hard disk drive (HDD), CD-ROM, and the like.

The first storage 240 may receive input data. For example, the first storage 240 may receive the input data from the detector 160. The input data may include a PCAR spectral matrix 30. The PCAR spectral matrix 30 may be generated using a first spectral image corresponding to a first PCA angle set and a first wavelength and a second spectral image corresponding to a second PCA angle set and a second wavelength different from the first wavelength. Each of the first PCA angle set and the second PCA angle set may include a first angle for adjusting a polarizing direction of incident light of the measurement sample, a second angle for adjusting a phase difference of the incident light, and a third angle for adjusting a polarizing direction of light reflected from the measurement sample, but aspects of the present inventive concept are not limited thereto. The first storage 240 may store a data analysis module for deducing PCA angle sets and wavelength bands under optimal conditions for measurement variables using the processor 230.

The deducing of the PCA angle sets and wavelength bands under optimal conditions for measurement variables may comprise deducing spectrums representing a change in the light intensity in each pixel depending on wavelengths using the PCAR spectral matrix 30, and selecting the PCA angle set and wavelength band under optimal conditions for measurement variables using the spectrums.

The selecting of the PCA angle set and wavelength band under optimal conditions for measurement variables may comprise selecting the PCA angle set and wavelength band under optimal or near optimal conditions using a correlation analysis algorithm for measuring a similarity between the spectrum extracted from the PCAR spectral matrix 30 and a predetermined value for the measurement variables or a principal component analysis algorithm for selecting the wavelength band having the largest displacement of the measurement variables in the extracted spectrum. Furthermore, the selecting of the PCA angle set and wavelength band under optimal conditions for measurement variables may comprise performing a rank test to determine whether the selected PCA angle sets or wavelength bands of the plurality of measurement variables overlap or not.

The second storage 250 may store the input data. The input data stored in the second storage 250 may be provided to the data analysis module stored in the first storage 240, but aspects of the present inventive concept are not limited thereto.

The data analysis device 202 may be electrically connected to a spectral ellipsometry measurement system including a polarizer 120, a compensator 130, an analyzer 140 and a detector 160, but aspects of the present inventive concept are not limited thereto.

A data analysis method of the above-described data analysis device 202 may be stored in a recording medium having a program stored therein, but aspects of the present inventive concept are not limited thereto.

Figure 12:
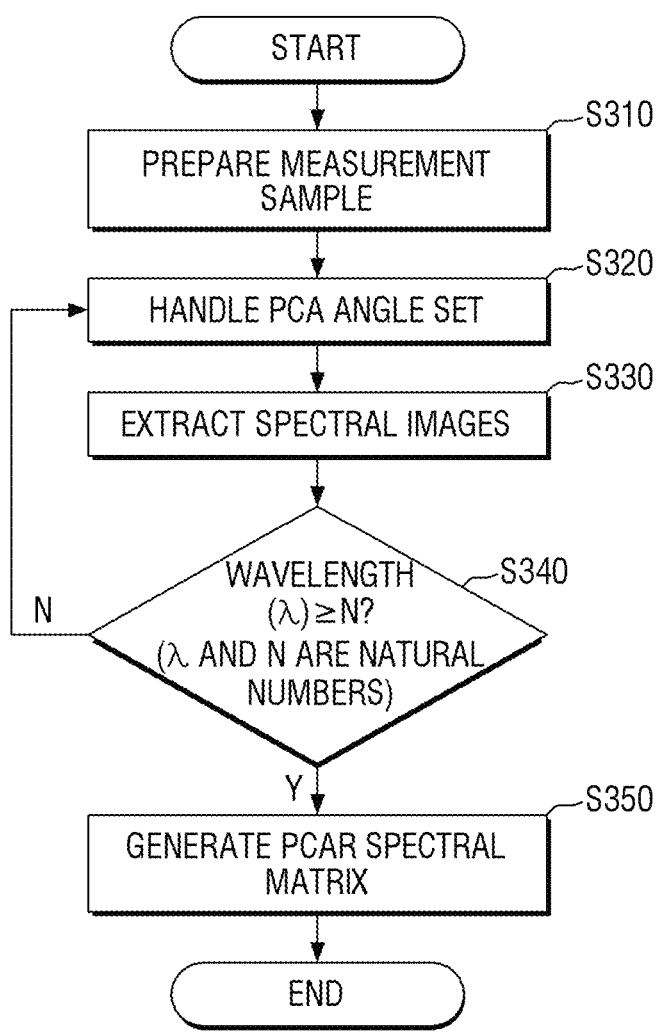
FIG. 12 is a flowchart illustrating operations of data analysis according to some embodiments of the present inventive concept.
Figure 13A:
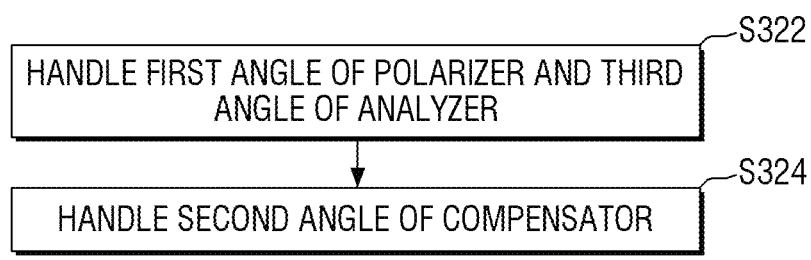
FIGS. 13A and 13B are flowcharts illustrating operations for handling PCA angle sets shown in FIG. 12 in accordance with some embodiments of the present inventive concept.
Figure 13B:
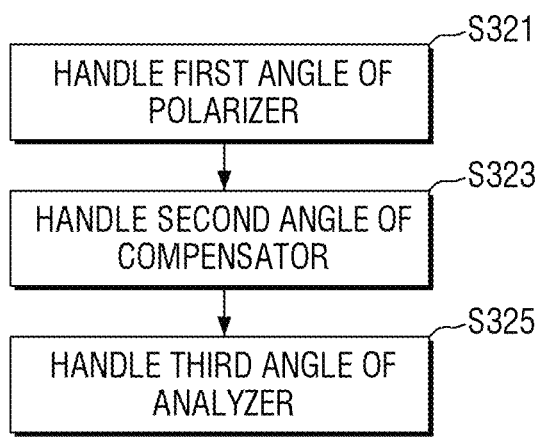

Referring now to FIG. 12 is a flowchart illustrating operations of data analysis according to some embodiments of the present inventive concept and FIGS. 13A and 13B are flowcharts illustrating operations for handling PCA angle sets illustrated in FIG. 12.

Referring first to FIG. 12, the data analysis method according to some embodiments of the present inventive concept begin at block S310 by preparing a measurement sample (S310). The measurement sample may have a predetermined value for measurement variables. The measurement variables may include critical dimension, a pattern height, recess, overlay, defect, and the like. For example, the measurement sample may be formed with a pattern having multiple heights, and the user may be provided with information concerning the respective heights, for example, spectrums, prior to measurement, but aspects of the present inventive concept are not limited thereto.

PCA angle sets may be handled (block S320). In particular, using the PCA angle sets including first to third angles, the first angle of a polarizer 120 adjusting a polarizing direction of incident light 55 of the measurement sample, the second angle of a compensator 130 adjusting a phase difference of the incident light 55, and the third angle of an analyzer 140 adjusting a polarizing direction of light reflected from the measurement sample may be handled. The controller 180 may receive the PCA angle sets from the processor 200 and may control the first to third angles. The PCA angle sets may be varied randomly or by a predetermined algorithm, but aspects of the present inventive concept are not limited thereto.

Spectral images are extracted (block S330). In particular, a first spectral image and a second spectral image may be extracted from the reflected light, the first spectral image corresponding to a first PCA angle set and a first wavelength and the second spectral image corresponding to a second PCA angle set and a second wavelength different from the first wavelength.

It is determined whether a magnitude of the wavelength is greater than a predetermined natural number N or not (block S340). If it is determined that the magnitude of the wavelength is greater than the predetermined natural number N (block S340), a PCAR spectral matrix is generated using the measured spectral images (block S350).

Conversely, if it is determined that the magnitude of the wavelength is smaller than the predetermined natural number N (block S340), the magnitude of the wavelength is increased to adjust the PCA angle sets and other spectral images are extracted. In such a manner, spectral images corresponding to wavelengths having magnitudes in a range of 0 to N may be extracted (operations return to block S320 and repeat).

In some embodiments, blocks S310 to S350 are repeatedly performed to form a plurality of PCAR spectral matrixes. For example, the generating of the plurality of PCAR spectral matrixes may comprise generating a first PCAR spectral matrix using the first and second spectral images and generating a second PCAR spectral matrix using a third PCA angle set different from the first PCA angle set, a third spectral image corresponding to the first wavelength, a fourth PCA angle set different from the second PCA angle set and a fourth spectral image corresponding to the second wavelength. In these embodiments, the PCA angle sets may be varied randomly or by a predetermined algorithm, but aspects of the present inventive concept are not limited thereto.

Referring now to FIG. 13A, the adjusting of the PCA angle sets in step S320 may include fixing the first angle of the polarizer 120 and the third angle of the analyzer 140 (S322). The second angle of the compensator 130 is handled (S324). If the handling of the second angle of the compensator 130 is completed, the process returns to step S322 to handle the second angle of the compensator 130 while fixing the first angle and the third angle at different angles, but aspects of the present inventive concept are not limited thereto.

Referring now to FIG. 13B, the adjusting of the PCA angle sets in step S320 includes handling the first angle of the polarizer 120 (S321). The second angle of the compensator 130 is handled (S323). The third angle of the analyzer 140 is handled (S325). In other words, the first to third angles may be sequentially handled, but aspects of the present inventive concept are not limited thereto. The order of performing steps S321 and S325 may be changed or steps S321 and S325 may be simultaneously performed, thereby forming combinations of the plurality of PCA angle sets.

Figure 14:
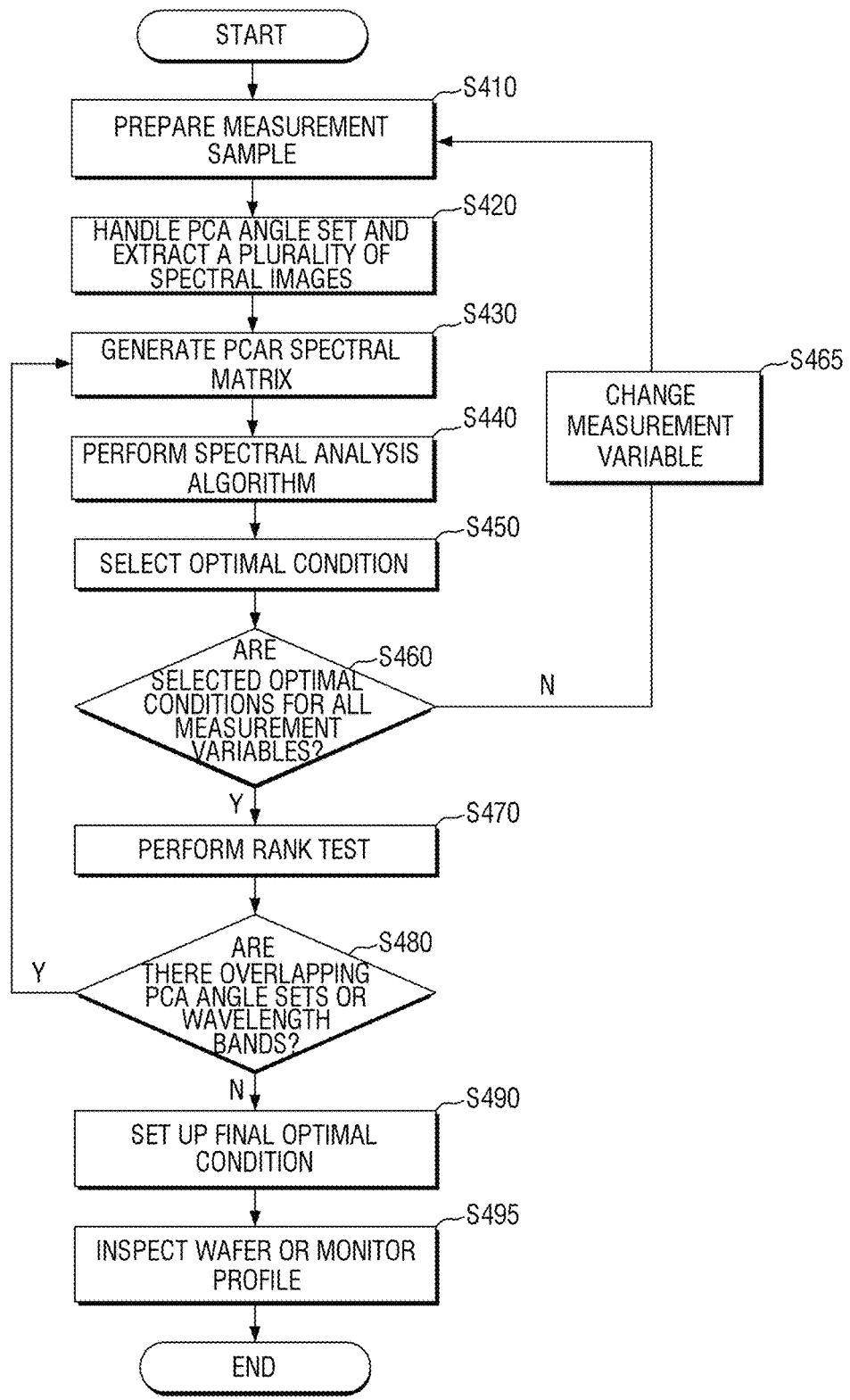
FIG. 14 is a flowchart illustrating operations for data analysis according to some embodiments of the present inventive concept.

Referring now to FIG. 14, a flowchart of a data analysis method according to some embodiments of the present inventive concept will be discussed. As illustrated in FIG. 14, operations begin by preparing a measurement sample having a predetermined value for measurement variables (block S410). PCA angle sets are adjusted to extract a plurality of spectral images (block S420). PCAR spectral matrixes are generated using the plurality of spectral images (block S430). blocks S410 to S430 may be performed in substantially the same manner with blocks S310 to S350 discussed above. Therefore, after performing steps S410 to S430, the plurality of PCAR spectral matrixes may be generated.

A spectrum analysis algorithm is performed (block S440). The spectrum analysis algorithm may be performed by a processor 200 or a data analysis device 202. In particular, spectrums representing a change in the light intensity depending on wavelengths in each pixel are generated using the PCAR spectral matrixes.

The PCA angle sets and wavelength bands under optimal or near optimal conditions for measurement variables are selected (block S450). It is determined whether the optimal conditions for all of the measurement variables are selected or not (block S460). If the optimal conditions for all of the measurement variables are not selected, blocks S410 to S450 are repeatedly performed on other measurement variables whose optimal conditions are yet to be selected.

Conversely, if the optimal conditions for all of the measurement variables are selected, a rank test is performed (block S470). In particular, if multiple measurement variables demonstrate the optimal sensitivity with respect to the selected PCA angle set and wavelength band under the same condition, the condition may be delicately readjusted to set up independent final conditions for the respective measurement variables. At this stage, the rank test may be employed.

As the result of the rank test, it is determined whether the selected PCA angle sets or wavelength bands overlap or not (block S480). As the result of the rank test, if the selected PCA angle sets or wavelength bands overlap, the spectrum analysis algorithm of block S440 is performed again to select the next PCA angle set and wavelength band to avoid interference among the measurement variables.

As the result of the rank test, if the selected PCA angle sets or wavelength bands for all of the measurement variables do not overlap, the final optimal condition for the PCA angle sets and wavelength band is set up (block S490).

Based on the PCA angle sets and wavelength bands under the optimal conditions for the measurement variables, different products from the measurement sample, resulting from the manufacturing process of the wafer 80, are inspected (block S495). In other words, since the PCA angle sets and wavelength bands under the optimal conditions for the measurement variables are used in inspecting the products resulting from the manufacturing process of the wafer 80 without performing separate simulation tests on the resulting products, a change in the measurement variables can be identified at a high speed.

Figure 15:
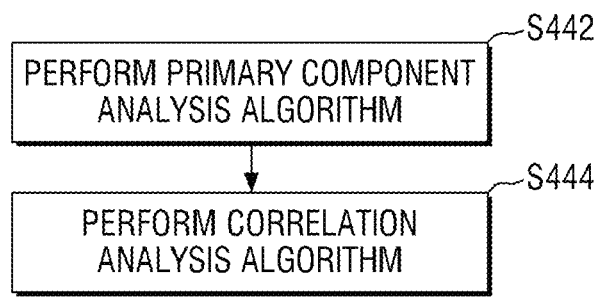
FIG. 15 is a flowchart illustrating operations for performing a spectrum analysis algorithm shown in FIG. 14 in accordance with some embodiments of the present inventive concept.
Figure 16:
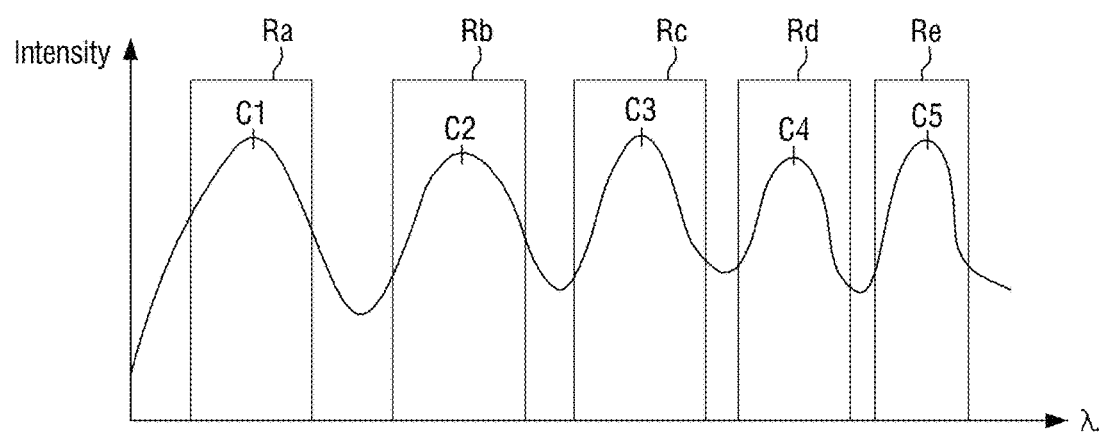
FIG. 16 is a graph illustrating a principal component analysis algorithm according to some embodiments of the present inventive concept.

Referring now to FIG. 15 is a flowchart illustrating operations for performing a spectrum analysis algorithm illustrated in FIG. 14. FIG. 16 is a graph illustrating a principal component analysis algorithm according to some embodiments of the present inventive concept. FIG. 17 is a graph illustrating a correlation analysis algorithm according to some embodiments of the present inventive concept.

As illustrated in FIG. 15, the performing of the spectrum analysis algorithm in block S440 comprises performing a principal component analysis algorithm (block S442) and performing a correlation analysis algorithm (block S444). In FIG. 15, blocks S442 and S444 sequentially performed are illustrated, but aspects of the present inventive concept are not limited thereto. The order of performing blocks S442 and S444 may be changed or blocks S442 and S444 may be simultaneously performed.

Referring now to FIG. 16, the principal component analysis algorithm may be used in selecting the wavelength band having the largest displacement of the measurement variables in the spectrum. The spectrums shown in FIG. 16 may have multiple peak values C1 to C5, which may represent principal components of the measurement variables, respectively. Therefore, the principal component analysis algorithm may be used in selecting the optimal wavelength band by determining in which one among wavelength bands Ra to Re of the spectrums the principal component reacting most sensitively to the measurement variables is positioned, but aspects of the present inventive concept are not limited thereto.

Referring now to FIG. 17, the correlation analysis algorithm may be performed for measuring a similarity between the spectrum extracted from the PCAR spectral matrix 30 and an ideal spectrum having a predetermined value (Sref) for the measurement variables. The user may hold the predetermined ideal spectrum value Sref prior to measurement. In other words, the measurement samples may be fabricated by the user to satisfy the ideal spectrum value Sref. The measurement sample may vary according to the measurement variable to be measured.

Therefore, the spectrum reacting most sensitively to the measurement variables may be selected by comparing the similarity between the spectrum extracted from the PCAR spectral matrix and the predetermined ideal spectrum value (Sref), but aspects of the present inventive concept are not limited thereto.

Figure 18:
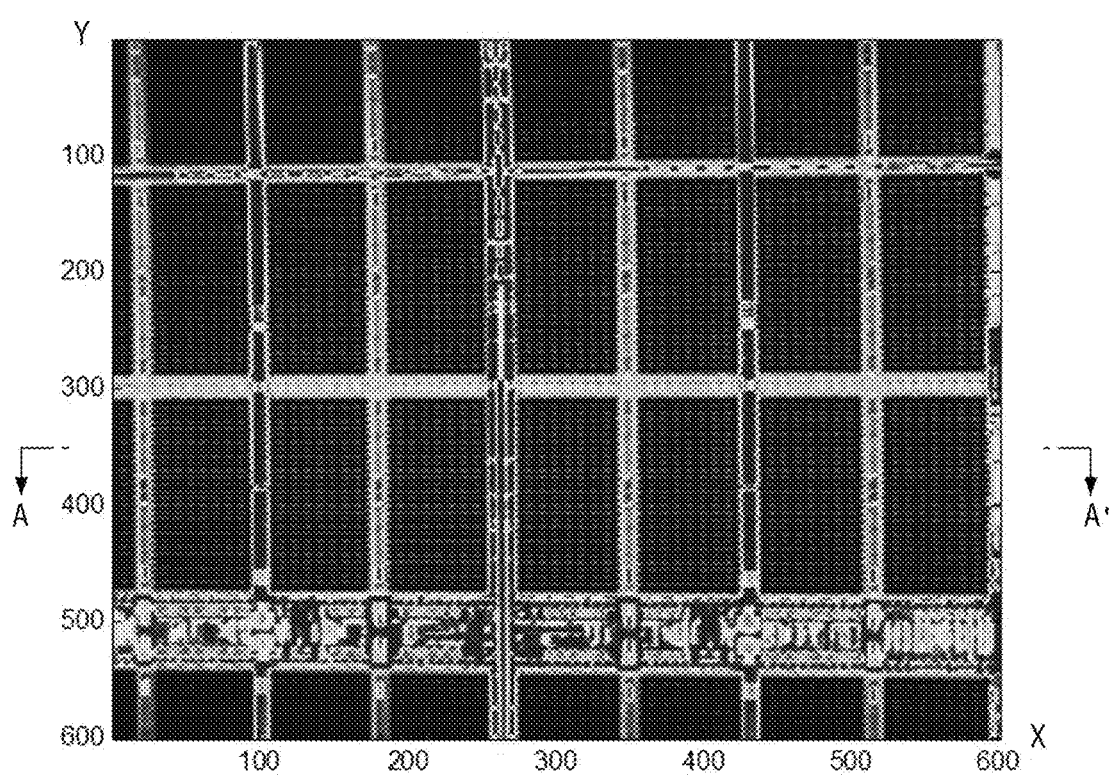
FIG. 18 is a diagram illustrating a layout view of a measurement sample measured by a spectral ellipsometry measurement system and method or a data analysis device according to some embodiments of the present inventive concept.
Figure 19:
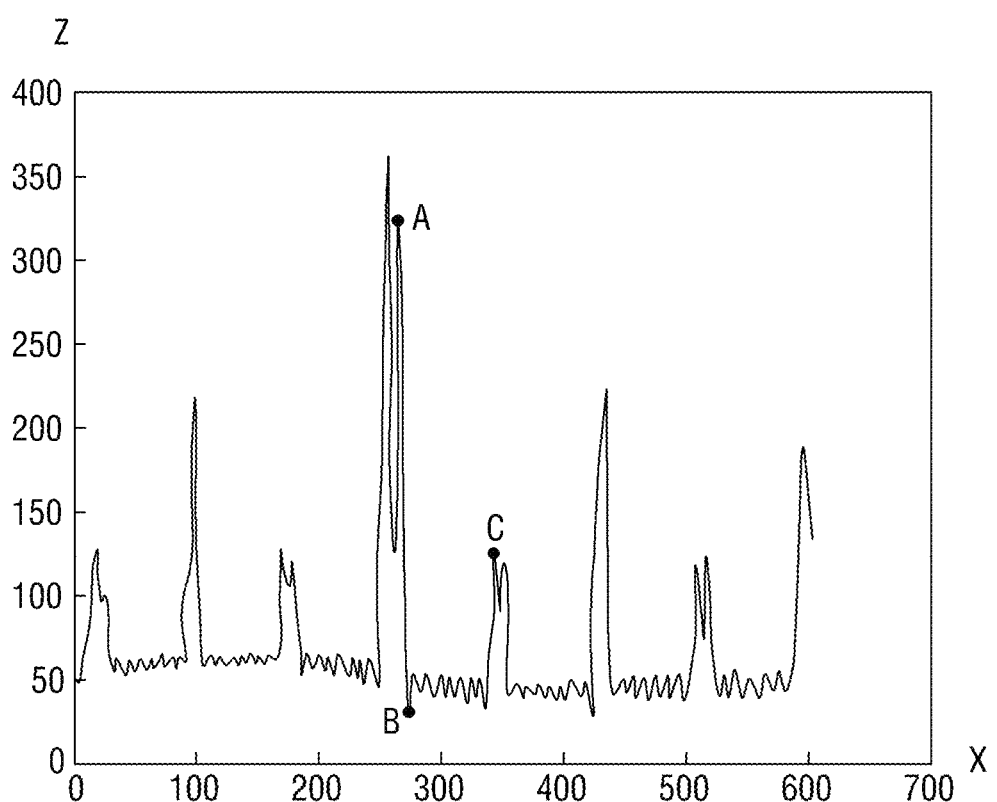
FIG. 19 is a cross-section taken along the line A-A' of FIG. 18, illustrating a measurement sample in accordance with some embodiments of the present inventive concept.
Figure 20:
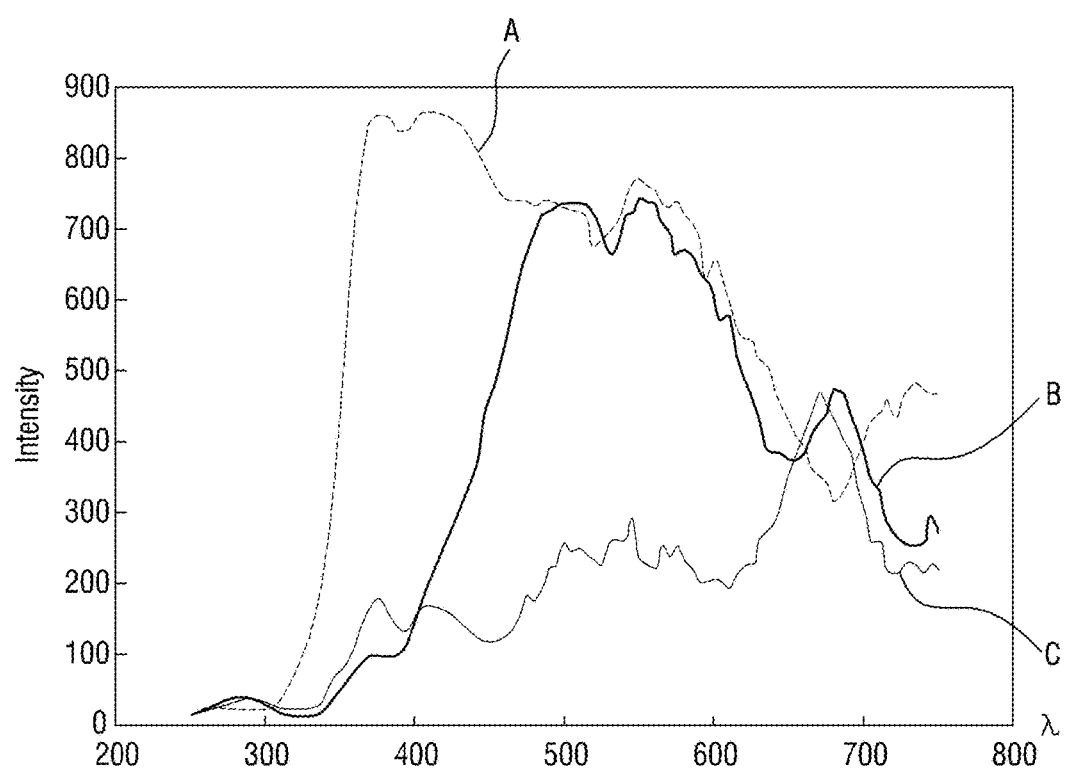
FIG. 20 is a graph illustrating spectrums of multiple points shown in FIG. 19 in accordance with some embodiments of the present inventive concept.

Referring now to FIG. 18 is a layout view of a measurement sample measured by a spectral ellipsometry measurement system and method or a data analysis device according to some embodiments of the present inventive concept. FIG. 19 is a cross-section taken along the line A-A' of FIG. 18, illustrating a measurement sample. FIG. 20 is a graph illustrating spectrums of multiple points shown in FIG. 19.

Referring first to FIG. 18, images measured with respect to spatial axes of spatial X and spatial Y for a pixel array of the measurement sample having multiple heights are illustrated.

Referring now to FIG. 19, a graph representing the measurement sample with respect to spatial axes of spatial X and spatial Z is illustrated. In FIG. 19, the spatial Z indicates heights of the measurement sample, taken along the line A-A'.

Referring to FIG. 20, a graph representing spectral images acquired under optimal PCA conditions is illustrated. As confirmed from the graph illustrated in FIG. 20, the spectrums for the measurement variables under the optimal or near optimal PCA conditions demonstrate a greatest change according to the height values. In other words, as illustrated in FIG. 20, different spectrums are shown at a point rather than a pattern area, at a line point in a pattern and at a space point in a pattern, the height values of the spectral images may be reconstructed through spectral analysis.

Therefore, independent conditions having highest correlation can be acquired for profiles to be measured using PCA angle based spectral analysis proposed in the spectral ellipsometry measurement system or method according to some embodiments of the present inventive concept. Furthermore, a profile change in the measurement variables within a wafer can be monitored at a high speed using pre-acquired conditions.

While the present inventive concept has been particularly shown and described with reference to exemplary embodiments thereof, it will be understood by those of ordinary skill in the art that various changes in form and details may be made therein without departing from the spirit and scope of the present inventive concept as defined by the following claims. It is therefore desired that the present embodiments be considered in all respects as illustrative and not restrictive, reference being made to the appended claims rather than the foregoing description to indicate the scope of the invention.

What is claimed is:

1. A spectral ellipsometry measurement system comprising:
   a polarizer that rotates at a first angle and adjusts a polarizing direction of incident light of a measurement sample;
   a compensator that rotates at a second angle, different from the first angle, and adjusts a phase difference of the incident light;
   an analyzer that rotates at a third angle and adjusts a polarizing direction of light reflected on the measurement sample;
   a detector that detects a spectral image from the reflected light;
   a controller that controls one of the polarizer, the compensator, and the analyzer according to polarizer-compensator-analyzer (PCA) angle sets including the first to third angles; and
   a processor that receives, from the detector, a first spectral image corresponding to a first PCA angle set and a first wavelength and a second spectral image corresponding to a second PCA angle set and a second wavelength, different from the first wavelength, and generates a polarizer-compensator-analyzer rotating (PCAR) spectral matrix using the first and second spectral images.

2. The system of claim 1, wherein the processor comprises:
   a first processing device that converts the first and second spectral images detected from the detector into the PCAR spectral matrix, stores the PCAR spectral matrix and generates spectrums representing a change in light intensity in each pixel based on wavelengths; and
   a second processing device that analyzes the spectrums generated in the first processing device and selects the PCA angle sets and wavelength bands for measurement variables.

3. The system of claim 2, wherein the first processing device stores a first PCAR spectral matrix and a second PCAR spectral matrix, different from the first PCAR spectral matrix, the first PCAR spectral matrix being generated using the first and second spectral images and the second PCAR spectral matrix being generated using a third PCA angle set, different from the first PCA angle set, a third spectral image corresponding to the first wavelength, a fourth PCA angle set, different from the second PCA angle set, and a fourth spectral image corresponding to the second wavelength.

4. The system of claim 2, wherein the second processing device performs one of:
a correlation analysis algorithm for measuring a similarity between spectrum extracted from the PCAR spectral matrix and an ideal spectrum; and
a principal component analysis algorithm for selecting the wavelength band having the largest displacement of the measurement variables in the extracted spectrum.

5. The system of claim 1, further comprising:
a light source irradiating incident light of a particular wavelength into a measuring area on the measurement sample; and
an imaging lens positioned between the analyzer and the detector that adjusts chromatic aberration of the reflected light.

6. The system of claim 5, wherein the polarizer is positioned between the light source and the compensator, a first lens is positioned between the compensator and the measurement sample, and a second lens is positioned between the measurement sample and the analyzer.

7. The system of claim 1, wherein the reflected light is incident on a photo sensor included in the detector positioned at an angle with respect to the reflected light that is not a right angle.

8. A method for spectral ellipsometry measurement, the method comprising:
providing a measurement sample having a predetermined value set with respect to measurement variables;
based on polarizer-compensator-analyzer (PCA) angle sets including first to third angles, handling the first angle of a polarizer adjusting a polarizing direction of incident light of the measurement sample, the second angle of a compensator adjusting a phase difference of the incident light, and the third angle of an analyzer adjusting a polarizing direction of light reflected from the measurement sample;
extracting a first spectral image and a second spectral image from the reflected light, the first spectral image corresponding to a first PCA angle set and a first wavelength and the second spectral image corresponding to a second PCA angle set and a second wavelength, different from the first wavelength; and
generating a polarizer-compensator-analyzer rotating (PCAR) spectral matrix using the first and second spectral images.

9. The method of claim 8, wherein generating the PCAR spectral matrix comprises:
generating a first PCAR spectral matrix using the first and second spectral images; and
generating a second PCAR spectral matrix using a third spectral image corresponding to a third PCA angle set, different from the first PCA angle set, and the first wavelength and a fourth spectral image corresponding to a fourth PCA angle set, different from the second PCA angle set, and the second wavelength.

10. The method of claim 9, further comprising one of:
varying the PCA angle sets randomly; and
varying the PCA angle sets using a predetermined algorithm.

11. The method of claim 8, further comprising:
generating spectrums representing a change in light intensity in each pixel depending on wavelengths using the PCAR spectral matrix; and
selecting the PCA angle set and wavelength band for the measurement variables through a spectrum analysis algorithm using the spectrums.

12. The method of claim 11, wherein the spectrum analysis algorithm includes a correlation analysis algorithm for measuring a similarity between the spectrum extracted from the PCAR spectral matrix and an ideal spectrum and a principal component analysis algorithm for selecting the wavelength band having the largest displacement of the measurement variables in the extracted spectrum.

13. The method of claim 11, wherein selecting the PCA angle set and wavelength band comprises selecting PCA angle sets and wavelength bands for a plurality of measurement variables.

14. The method of claim 13, wherein selecting the PCA angle set and wavelength band comprises performing a rank test to determine whether the selected PCA angle sets or wavelength bands of the plurality of measurement variables overlap.

15. The method of claim 11, wherein the measurement variables comprise one of a critical dimension, a pattern's height, a recess, an overlay and a defect.

16. A spectral ellipsometry measurement system comprising:
a polarizer that rotates at a first angle and adjusts a polarizing direction of incident light of a measurement sample;
compensator that rotates at a second angle, different from the first angle, and adjusts a phase difference of the incident light;
an analyzer that rotates at a third angle and adjusts a polarizing direction of light reflected on the measurement sample;
a controller that controls one of the polarizer, the compensator, and the analyzer according to polarizer-compensator-analyzer (PCA) angle sets including the first to third angles; and
a processor that receives, from a detector, a first spectral image corresponding to a first PCA angle set and a first wavelength and a second spectral image corresponding to a second PCA angle set and a second wavelength, different from the first wavelength, and generates a polarizer-compensator-analyzer rotating (PCAR) spectral matrix using the first and second spectral images.

* * * * *